United States Patent
Freese et al.

(10) Patent No.: US 9,383,307 B2
(45) Date of Patent: *Jul. 5, 2016

(54) METHODS AND DEVICES FOR OPTICALLY DETERMINING A CHARACTERISTIC OF A SUBSTANCE

(75) Inventors: Robert Freese, Pittsboro, NC (US); Christopher Michael Jones, Houston, TX (US); David Perkins, The Woodlands, TX (US); Michael Simcock, Columbia, SC (US); William Soltmann, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 772 days.

This patent is subject to a terminal disclaimer.

(21) Appl. No.: 13/456,302

(22) Filed: Apr. 26, 2012

(65) Prior Publication Data

US 2013/0284897 A1 Oct. 31, 2013

(51) Int. Cl.
*G01N 21/27* (2006.01)
*G01J 3/36* (2006.01)
*G01N 21/31* (2006.01)
*G06E 3/00* (2006.01)
*G01J 3/42* (2006.01)
(Continued)

(52) U.S. Cl.
CPC . *G01N 21/27* (2013.01); *G01J 3/36* (2013.01); *G01J 3/42* (2013.01); *G01N 21/31* (2013.01); *G06E 3/001* (2013.01); *G01J 3/0232* (2013.01); *G01J 2003/1213* (2013.01)

(58) Field of Classification Search
CPC ... G01N 21/27; G01N 21/31; G01N 21/3577; G01N 21/15; G01N 21/17; G01N 21/85; G01N 27/3271; G01N 33/2823; G01J 3/36; G01J 3/42; G01J 3/0232; G01J 2003/1213; G06E 3/001

See application file for complete search history.

(56) References Cited

U.S. PATENT DOCUMENTS 3,488,491 A 1/1970 Schuman
4,761,073 A 8/1988 Meltz et al.
(Continued)

FOREIGN PATENT DOCUMENTS

EP 1969326 9/2008
EP 2087328 8/2009
(Continued)

OTHER PUBLICATIONS

Halliburton Brochure for "Acid-on-the-Fly (AOF) Blending System," published 2009.
(Continued)

*Primary Examiner* — John Lee
(74) *Attorney, Agent, or Firm* — McDermott Will & Emery LLP; Craig Roddy

(57) ABSTRACT

Optical computing devices are disclosed. One exemplary optical computing device includes an electromagnetic radiation source configured to optically interact with a sample and at least two integrated computational elements. The at least two integrated computational elements are configured to produce optically interacted light and further configured to be associated with a characteristic of the sample. The optical computing device further includes a first detector arranged to receive the optically interacted light from the at least two integrated computational elements and thereby generate a first signal corresponding to the characteristic of the sample.

12 Claims, 5 Drawing Sheets

(51) Int. Cl.
*G01J 3/12* (2006.01)
*G01J 3/02* (2006.01)

(56) References Cited

U.S. PATENT DOCUMENTS

| | | | |
|---|---|---|---|
| 4,795,262 A | 1/1989 | Morris et al. | |
| 4,806,012 A | 2/1989 | Meltz et al. | |
| 4,882,492 A | 11/1989 | Schlager | |
| 5,399,854 A | 3/1995 | Dunphy et al. | |
| 5,493,390 A | 2/1996 | Varasi et al. | |
| 5,737,076 A | 4/1998 | Glaus et al. | |
| 6,091,504 A | 7/2000 | Walker et al. | |
| 6,198,531 B1 | 3/2001 | Myrick et al. | |
| 6,268,911 B1 | 7/2001 | Tubel et al. | |
| 6,529,276 B1 | 3/2003 | Myrick | |
| 6,576,188 B1 | 6/2003 | Rose et al. | |
| 7,123,844 B2 | 10/2006 | Myrick | |
| 7,138,156 B1 | 11/2006 | Myrick et al. | |
| 7,332,094 B2 | 2/2008 | Abney et al. | |
| 7,472,748 B2 | 1/2009 | Gdanski et al. | |
| 7,623,233 B2 | 11/2009 | Freese et al. | |
| 7,671,973 B2 * | 3/2010 | Van Beek et al. | 356/39 |
| 7,697,141 B2 | 4/2010 | Jones et al. | |
| 7,712,527 B2 | 5/2010 | Roddy | |
| 7,834,999 B2 | 11/2010 | Myrick et al. | |
| 7,911,605 B2 | 3/2011 | Myrick et al. | |
| 7,920,258 B2 | 4/2011 | Myrick et al. | |
| 7,934,556 B2 | 5/2011 | Clark et al. | |
| 8,049,881 B2 * | 11/2011 | Myrick et al. | 356/303 |
| 8,141,633 B2 | 3/2012 | Hampton et al. | |
| 8,253,619 B2 | 8/2012 | Holbrook et al. | |
| 8,345,234 B2 | 1/2013 | Myrick et al. | |
| 8,547,556 B2 | 10/2013 | Irani | |
| 8,780,352 B2 | 7/2014 | Freese et al. | |
| 8,823,939 B2 * | 9/2014 | Freese et al. | 356/433 |
| 8,879,053 B2 | 11/2014 | Freese et al. | |
| 8,908,165 B2 | 12/2014 | Tunheim et al. | |
| 8,912,477 B2 * | 12/2014 | Freese et al. | 250/208.2 |
| 8,941,046 B2 | 1/2015 | Freese et al. | |
| 8,960,294 B2 | 2/2015 | Freese et al. | |
| 8,997,860 B2 | 4/2015 | Freese et al. | |
| 9,013,698 B2 | 4/2015 | Freese et al. | |
| 9,013,702 B2 | 4/2015 | Freese et al. | |
| 9,103,716 B2 * | 8/2015 | Tunheim | G01J 3/0264 |
| 9,103,720 B2 * | 8/2015 | Russell | C09K 8/035 |
| 9,103,767 B2 * | 8/2015 | Freese | G01N 21/17 |
| 9,142,002 B2 * | 9/2015 | Dutton | G06T 1/20 |
| 9,170,154 B2 * | 10/2015 | Myrick | G01J 3/02 |
| 9,170,208 B2 * | 10/2015 | Tunheim | G01J 3/0218 |
| 9,176,052 B2 * | 11/2015 | Tunheim | G01N 21/31 |
| 9,182,282 B2 * | 11/2015 | Myrick | G01J 3/02 |
| 9,182,355 B2 * | 11/2015 | Tunheim | G01N 21/85 |
| 9,206,386 B2 * | 12/2015 | Tunheim | C12M 41/36 |
| 2001/0020675 A1 | 9/2001 | Tubel et al. | |
| 2002/0023752 A1 | 2/2002 | Qu et al. | |
| 2002/0071121 A1 | 6/2002 | Ortyn et al. | |
| 2002/0109080 A1 | 8/2002 | Tubel et al. | |
| 2003/0056581 A1 | 3/2003 | Turner et al. | |
| 2003/0145988 A1 | 8/2003 | Mullins et al. | |
| 2004/0045705 A1 | 3/2004 | Gardner et al. | |
| 2004/0129884 A1 | 7/2004 | Boyle et al. | |
| 2006/0102343 A1 | 5/2006 | Skinner et al. | |
| 2006/0142955 A1 | 6/2006 | Jones et al. | |
| 2006/0158734 A1 * | 7/2006 | Schuurmans et al. | 359/485 |
| 2006/0183183 A1 | 8/2006 | Felkner et al. | |
| 2007/0177240 A1 * | 8/2007 | Van Beek et al. | 359/197 |
| 2007/0248488 A1 | 10/2007 | Denkewicz | |
| 2007/0282647 A1 | 12/2007 | Freese et al. | |
| 2007/0291251 A1 * | 12/2007 | Rensen et al. | 356/39 |
| 2008/0041594 A1 | 2/2008 | Boles et al. | |
| 2008/0094623 A1 * | 4/2008 | Schuurmans et al. | 356/306 |
| 2008/0133193 A1 | 6/2008 | Gdanski et al. | |
| 2008/0231849 A1 | 9/2008 | Myrick et al. | |
| 2008/0276687 A1 | 11/2008 | Myrick et al. | |
| 2008/0309930 A1 * | 12/2008 | Rensen | 356/300 |
| 2009/0002697 A1 | 1/2009 | Freese et al. | |
| 2009/0015819 A1 | 1/2009 | Van Beek et al. | |
| 2009/0033933 A1 | 2/2009 | Myrick et al. | |
| 2009/0073433 A1 | 3/2009 | Myrick et al. | |
| 2009/0087912 A1 | 4/2009 | Ramos et al. | |
| 2009/0097024 A1 | 4/2009 | Blackburn et al. | |
| 2009/0137887 A1 | 5/2009 | Shariati et al. | |
| 2009/0140144 A1 | 6/2009 | Myrick et al. | |
| 2009/0154288 A1 | 6/2009 | Heathman | |
| 2009/0182693 A1 | 7/2009 | Fulton et al. | |
| 2009/0205821 A1 | 8/2009 | Smith | |
| 2009/0216504 A1 | 8/2009 | Priore et al. | |
| 2009/0219512 A1 | 9/2009 | Myrick et al. | |
| 2009/0219538 A1 | 9/2009 | Myrick et al. | |
| 2009/0219539 A1 | 9/2009 | Myrick et al. | |
| 2009/0245718 A1 | 10/2009 | Li et al. | |
| 2009/0250613 A1 | 10/2009 | Myrick et al. | |
| 2009/0299946 A1 | 12/2009 | Myrick et al. | |
| 2009/0305330 A1 | 12/2009 | Kroon et al. | |
| 2009/0316150 A1 | 12/2009 | Myrick et al. | |
| 2010/0006292 A1 | 1/2010 | Boles et al. | |
| 2010/0042348 A1 | 2/2010 | Bakker | |
| 2010/0050905 A1 | 3/2010 | Lewis et al. | |
| 2010/0051266 A1 | 3/2010 | Roddy et al. | |
| 2010/0051275 A1 | 3/2010 | Lewis et al. | |
| 2010/0073666 A1 | 3/2010 | Perkins et al. | |
| 2010/0084132 A1 | 4/2010 | Noya et al. | |
| 2010/0141952 A1 | 6/2010 | Myrick et al. | |
| 2010/0148785 A1 | 6/2010 | Schaefer et al. | |
| 2010/0149523 A1 | 6/2010 | Heideman et al. | |
| 2010/0149537 A1 | 6/2010 | Myrick et al. | |
| 2010/0153048 A1 | 6/2010 | Myrick et al. | |
| 2010/0182600 A1 | 7/2010 | Freese et al. | |
| 2010/0195105 A1 | 8/2010 | Myrick et al. | |
| 2010/0245096 A1 | 9/2010 | Jones et al. | |
| 2010/0265509 A1 | 10/2010 | Jones et al. | |
| 2010/0302539 A1 | 12/2010 | Myrick et al. | |
| 2010/0305741 A1 | 12/2010 | Myrick | |
| 2010/0326659 A1 | 12/2010 | Schultz et al. | |
| 2010/0328669 A1 | 12/2010 | Myrick et al. | |
| 2011/0048708 A1 | 3/2011 | Glasbergen et al. | |
| 2011/0063086 A1 | 3/2011 | Oishi | |
| 2011/0163046 A1 | 7/2011 | Neal et al. | |
| 2011/0197662 A1 | 8/2011 | McAlister | |
| 2011/0199610 A1 | 8/2011 | Myrick et al. | |
| 2012/0211650 A1 | 8/2012 | Jones et al. | |
| 2012/0250017 A1 | 10/2012 | Morys et al. | |
| 2013/0031964 A1 | 2/2013 | Tunheim et al. | |
| 2013/0031970 A1 | 2/2013 | Freese et al. | |
| 2013/0031971 A1 | 2/2013 | Freese et al. | |
| 2013/0031972 A1 | 2/2013 | Freese et al. | |
| 2013/0032333 A1 | 2/2013 | Freese et al. | |
| 2013/0032340 A1 | 2/2013 | Freese et al. | |
| 2013/0033701 A1 * | 2/2013 | Tunheim et al. | 356/73 |
| 2013/0033702 A1 * | 2/2013 | Tunheim et al. | 356/73 |
| 2013/0034842 A1 | 2/2013 | Tunheim et al. | |
| 2013/0284894 A1 | 10/2013 | Freese et al. | |
| 2013/0284895 A1 | 10/2013 | Freese et al. | |
| 2013/0284896 A1 | 10/2013 | Freese et al. | |
| 2013/0284897 A1 | 10/2013 | Freese et al. | |
| 2013/0284898 A1 | 10/2013 | Freese et al. | |
| 2013/0284899 A1 | 10/2013 | Freese et al. | |
| 2013/0284900 A1 | 10/2013 | Freese et al. | |
| 2013/0284901 A1 | 10/2013 | Freese et al. | |
| 2013/0284904 A1 | 10/2013 | Freese et al. | |
| 2013/0286398 A1 | 10/2013 | Freese et al. | |
| 2013/0286399 A1 | 10/2013 | Freese et al. | |
| 2013/0287061 A1 | 10/2013 | Freese et al. | |
| 2014/0263974 A1 * | 9/2014 | Freese et al. | 250/208.2 |
| 2014/0306096 A1 | 10/2014 | Freese et al. | |
| 2015/0015884 A1 * | 1/2015 | Russell | C09K 8/035 356/402 |
| 2015/0167456 A1 * | 6/2015 | Irani | E21B 47/102 73/152.23 |
| 2015/0212232 A1 * | 7/2015 | Perkins | E21B 49/087 73/152.18 |
| 2015/0241337 A1 * | 8/2015 | Talabi | G01N 21/359 705/306 |

(56) References Cited

U.S. PATENT DOCUMENTS

| | | | | |
|---|---|---|---|---|
| 2015/0260703 | A1* | 9/2015 | Mitchell | E21B 47/00 |
| | | | | 73/19.09 |
| 2015/0293013 | A1* | 10/2015 | Tunheim | G01N 21/75 |
| | | | | 435/39 |
| 2015/0300945 | A1* | 10/2015 | Gao | G01N 21/274 |
| | | | | 702/104 |
| 2015/0330215 | A1* | 11/2015 | Jamison | E21B 47/102 |
| | | | | 73/152.42 |
| 2015/0346084 | A1* | 12/2015 | Russell | G01N 21/31 |
| | | | | 356/402 |

FOREIGN PATENT DOCUMENTS

| | | |
|---|---|---|
| EP | 2140238 | 1/2010 |
| EP | 2320027 A1 | 5/2011 |
| GB | 2353310 A | 2/2001 |
| WO | 2004018840 A1 | 3/2004 |
| WO | 2004057285 A1 | 7/2004 |
| WO | 2006137902 | 12/2006 |
| WO | 2007064575 | 6/2007 |
| WO | 2007098392 A2 | 8/2007 |
| WO | 2008057912 A2 | 5/2008 |
| WO | 2011063086 A1 | 5/2011 |
| WO | 2013162744 A1 | 10/2013 |
| WO | 2013162787 A1 | 10/2013 |
| WO | 2013162795 A1 | 10/2013 |
| WO | 2013162799 A1 | 10/2013 |
| WO | 2013162809 A1 | 10/2013 |
| WO | 2013162860 A1 | 10/2013 |
| WO | 2013162861 A1 | 10/2013 |
| WO | 2013162901 A1 | 10/2013 |
| WO | 2013162906 A1 | 10/2013 |
| WO | 2013162913 A1 | 10/2013 |
| WO | 2013162914 A1 | 10/2013 |

OTHER PUBLICATIONS

Official Action for Canadian Patent Application No. 2,842,703 dated Jul. 25, 2014.

Myrick, et al. "Spectral Tolerance Determination for Multivariate Optical Element Design," Fresenuis' Journal of Analytical Chemistry, 369:2001; pp. 351-355.

Gdanski et al., "A New Model for Matching Fracturing Fluid Flowback Composition," 2007 SPE Hydraulic Fracturing Technology Conference held in College Station, Texas, SPE 106040.

Gdanski et al., "Using Lines-of-Solutions to Understand Fracture Conductivity and Fracture Cleanup," SPE 142096.

Myrick et al., "Application of Multivariate Optical Computing to Simple Near-Infrared Point Measurements," Proceedings of SPIE, US, vol. 4574, 2002, pp. 208-215, XP002391230.

Nelson et al., "Multivariate Optical Computation for Predictive Spectroscopy," Analytical Chemistry, vol. 70, No. 1, 1998, pp. 73-82, XP055067630.

Bialkowski, "Species Discrimination and Quantitative Estimation Using Incoherent Linear Optical Signal Processing of Emission Signals," Analytical Chemistry, vol. 58, No. 12, 1986, pp. 2561-2563, XP055067237.

Medendorp, et al., "Applications of Interated Sensing and Processing in Spectroscopic Imaging and Sensing," Journal of Chemometrics, vol. 19, No. 10, 2006, pp. 533-542, XP055067235.

Bin Dai et al., "Molecular Factor Computing for Predictive Spectroscopy," Pharmaceutical Research, Kluwer Academic Publishers-Plenum Publishers, NL, vol. 24, No. 8, 2007, pp. 1441-1449, XP019507244.

International Search Report and Written Opinion for PCT/US2013/036177 dated Jun. 28, 2013.

International Search Report and Written Opinion for PCT/US2013/036107 dated Jun. 28, 2013.

International Search Report and Written Opinion for PCT/US2013/033975 dated Jun. 28, 2013.

International Search Report and Written Opinion for PCT/US2013/035572 dated Jun. 28, 2013.

International Search Report and Written Opinion for PCT/US2013035604 dated Jun. 28, 2013.

International Search Report and Written Opinion for PCT/US2013/031467 dated Jun. 28, 2013.

International Search Report and Writen Opinion for PCT/US2013/031960 dated Jun. 28, 2013.

International Search Report and Written Opinion for PCT/US2013/032970 dated Jun. 28, 2013.

International Search Report and Written Opinion for PCT/US2013/033256 dated Jun. 28, 2013.

International Search Report and Written Opinion for PCT/US2013/033502 dated Jun. 28, 2013.

Applied Optics, vol. 35, pp. 5484-5492, 1996 and Vlo. 29, pp. 2876-2893, 1990.

Dobrowolski et al., "Refinement of Optical Multilayer Systems with Different Optimization Procedures," Applied Optics, Vo. 29, No. 19, 1990.

Official Action for Australian Patent Application No. 2013 252841 dated Nov. 10, 2014.

Official Action for Australian Patent Application No. 2013 252881 dated Nov. 12, 2014.

Official Action for Australian Patent Application No. 2013252855 dated Apr. 15, 2015.

Dai et al., Molecular Factor Computing for Predictive Spectroscopy, Pharmaceutical Research, vol. 24, No. 8, 2007, pp. 1441-1449.

Mendendorp J., et al., Application of Integrated Sensing and Processing in Spectroscopic Imaging and Sensing, Journal of Chemometrics, vol. 19, 2005, pp. 533-542.

Official Action for Australian Patent Application No. 2013252890 dated Jul. 11, 2015.

* cited by examiner

METHODS AND DEVICES FOR OPTICALLY DETERMINING A CHARACTERISTIC OF A SUBSTANCE

BACKGROUND

The present invention generally relates to systems and methods of optical computing and, more specifically, to systems and methods of determining a particular characteristic of a substance using two or more integrated computational elements.

Spectroscopic techniques for measuring various characteristics of materials are well known and are routinely used under laboratory conditions. In some cases, these spectroscopic techniques can be carried out without using an involved sample preparation. It is more common, however, to carry out various sample preparation procedures before conducting the analysis. Reasons for conducting sample preparation procedures can include, for example, removing interfering background materials from the analyte of interest, converting the analyte of interest into a chemical form that can be better detected by a chosen spectroscopic technique, and adding standards to improve the accuracy of quantitative measurements. Thus, there is usually a delay in obtaining an analysis due to sample preparation time, even discounting the transit time of transporting the sample to a laboratory.

Although spectroscopic techniques can, at least in principle, be conducted at a job site, such as a well site, or in a process, the foregoing concerns regarding sample preparation times can still apply. Furthermore, the transitioning of spectroscopic instruments from a laboratory into a field or process environment can be expensive and complex. Reasons for these issues can include, for example, the need to overcome inconsistent temperature, humidity, and vibration encountered during field use. Furthermore, sample preparation, when required, can be difficult under field analysis conditions. The difficulty of performing sample preparation in the field can be especially problematic in the presence of interfering materials, which can further complicate conventional spectroscopic analyses. Quantitative spectroscopic measurements can be particularly challenging in both field and laboratory settings due to the need for precision and accuracy in sample preparation and spectral interpretation.

SUMMARY OF THE INVENTION

The present invention generally relates to systems and methods of optical computing and, more specifically, to systems and methods of determining a particular characteristic of a substance using two or more integrated computational elements.

In one embodiment, the present invention provides a device including an electromagnetic radiation source configured to optically interact with a sample and at least two integrated computational elements. The at least two integrated computational elements may be configured to produce optically interacted light and may further be configured to be associated with a characteristic of the sample. The device may also include at least one detector arranged to receive the optically interacted light from the at least two integrated computational elements and thereby generate a first signal and a second signal. The first and second signals may then be computationally combined to determine the characteristic of the sample.

In another embodiment, a method of determining a characteristic of a sample is disclosed. The method may include optically interacting an electromagnetic radiation source with the sample and at least two integrated computational elements, and producing optically interacted light from the at least two integrated computational elements. The at least two integrated computational elements may each be configured to be associated with the characteristic of the sample. The method may also include receiving with at least one detector the optically interacted light from the at least two integrated computational elements, thereby generating a first signal and a second signal, and computationally combining the first and second signals to determine the characteristic of the sample.

In another aspect of the disclosure, another device is disclosed and may include an electromagnetic radiation source configured to optically interact with a sample and at least two integrated computational elements. The at least two integrated computational elements may be configured to produce optically interacted light and may further be configured to be associated with a characteristic of the sample. The device may also include a first detector arranged to receive the optically interacted light from the at least two integrated computational elements and thereby generate a first signal corresponding to the characteristic of the sample.

In yet another aspect of the disclosure, another method of determining a characteristic of a sample is disclosed. The method may include optically interacting an electromagnetic radiation source with a sample and at least two integrated computational elements, and producing optically interacted light from the at least two integrated computational elements. The at least two integrated computational elements may each be configured to be associated with the characteristic of the sample. The method may also include receiving with at least one detector the optically interacted light from the at least two integrated computational elements, thereby generating a first signal corresponding to the characteristic of the sample.

In yet another aspect of the disclosure, another device is disclosed and may include at least two integrated computational elements configured to receive electromagnetic radiation emitted from a sample and produce optically interacted light. The at least two integrated computational elements may be configured to be associated with a characteristic of the sample. The device may also include at least one detector arranged to receive the optically interacted light from the at least two integrated computational elements and thereby generate a first signal and a second signal. The first and second signals may be subsequently computationally combined to determine the characteristic of the sample.

In yet another aspect of the disclosure, another method of determining a characteristic of a sample is disclosed. The method may include optically interacting electromagnetic radiation radiated from the sample with at least two integrated computational elements, and producing optically interacted light from the at least two integrated computational elements. The at least two integrated computational elements may each be configured to be associated with the characteristic of the sample. The method may also include receiving with at least one detector the optically interacted light from the at least two integrated computational elements, thereby generating a first signal corresponding to the characteristic of the sample.

The features and advantages of the present invention will be readily apparent to one having ordinary skill in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is

DETAILED DESCRIPTION

Figure 1:
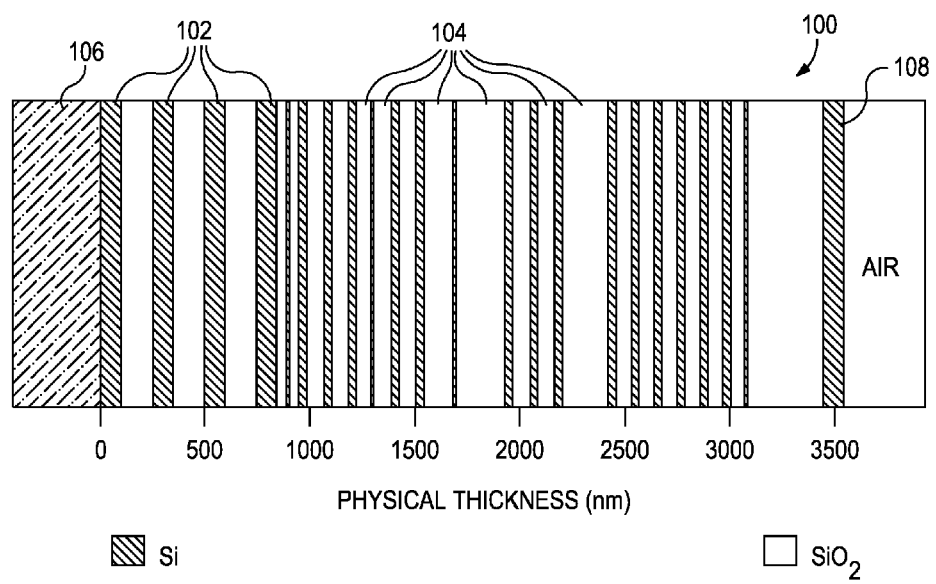
FIG. 1 illustrates an exemplary integrated computation element, according to one or more embodiments.

The present invention generally relates to systems and methods of optical computing and, more specifically, to systems and methods of determining a particular characteristic of a substance using two or more integrated computational elements.

Embodiments described herein include various configurations of optical computing devices, also commonly referred to as "opticoanalytical devices." The various embodiments of the disclosed optical computing devices may be suitable for use in the oil and gas industry. For example, embodiments disclosed herein provide systems and/or devices capable of providing a relatively low cost, rugged, and accurate system for monitoring petroleum quality for the purpose of optimizing decision-making at a well site to facilitate the efficient management of hydrocarbon production. Embodiments disclosed herein may also be useful in determining concentrations of various analytes of interest in any fluid present within a wellbore. It will be appreciated, however, that the various disclosed systems and devices are equally applicable to other technology fields including, but not limited to, the food and drug industry, industrial applications, mining industries, or any field where it may be advantageous to determine in real-time the concentrations of a specific characteristic or analyte of interest of a compound or material.

As used herein, the term "fluid" refers to any substance that is capable of flowing, including particulate solids, liquids, gases, slurries, emulsions, powders, muds, glasses, combinations thereof, and the like. In some embodiments, the fluid can be an aqueous fluid, including water or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid or a formation fluid. Fluids can include various flowable mixtures of solids, liquids and/or gases. Illustrative gases that can be considered fluids according to the present embodiments include, for example, air, nitrogen, carbon dioxide, argon, helium, hydrogen disulfide, mercaptan, thiophene, methane, ethane, butane, and other hydrocarbon gases, combinations thereof and/or the like.

As used herein, the term "characteristic" refers to a chemical, mechanical, or physical property of a substance. A characteristic of a substance may include a quantitative value of one or more chemical components therein. Such chemical components may be referred to herein as "analytes." Illustrative characteristics of a substance that can be monitored with the optical computing devices disclosed herein can include, for example, chemical composition e.g., identity and concentration, in total or of individual components, impurity content, pH, viscosity, density, ionic strength, total dissolved solids, salt content, porosity, opacity, bacteria content, combinations thereof, and the like.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation from a substance or sample of the substance, and produce an output of electromagnetic radiation from a processing element. The processing element may be, for example, an integrated computational element. The electromagnetic radiation emanating from the processing element is changed in some way so as to be readable by a detector, such that an output of the detector can be correlated to at least one characteristic of the substance. The output of electromagnetic radiation from the processing element can be reflected electromagnetic radiation, transmitted electromagnetic radiation, and/or dispersed electromagnetic radiation. As will be appreciated by those skilled in the art, whether reflected or transmitted electromagnetic radiation is analyzed by the detector may be dictated by the structural parameters of the optical computing device as well as other considerations known to those skilled in the art. In addition, emission and/or scattering of the substance, for example via fluorescence, luminescence, Raman scattering, and/or Raleigh scattering can also be monitored by the optical computing devices.

As used herein, the term "optically interact" or variations thereof refers to the reflection, transmission, scattering, diffraction, or absorption of electromagnetic radiation either on, through, or from one or more processing elements, such as integrated computational elements. Accordingly, optically interacted light refers to light that has been reflected, transmitted, scattered, diffracted, or absorbed by, emitted, or re-radiated, for example, using the integrated computational elements, but may also apply to interaction with a sample substance.

As used herein, the term "sample," or variations thereof, refers to at least a portion of a substance of interest to be tested or otherwise evaluated using the optical computing devices described herein. The sample includes the characteristic of interest, as defined above, and may be any fluid, as defined herein, or otherwise any solid substance or material such as, but not limited to, rock formations, concrete, other solid surfaces, etc.

At the very least, the exemplary optical computing devices disclosed herein will each include an electromagnetic radiation source, at least two processing elements (e.g., integrated computational elements), and at least one detector arranged to receive optically interacted light from the at least two processing elements. As disclosed below, however, in at least one embodiment, the electromagnetic radiation source may be omitted and instead the electromagnetic radiation may be derived from the substance or the sample of the substance itself. In some embodiments, the exemplary optical computing devices may be specifically configured for detecting, analyzing, and quantitatively measuring a particular characteristic or analyte of interest of a given sample or substance. In other embodiments, the exemplary optical computing devices may be general purpose optical devices, with post-acquisition processing (e.g., through computer means) being used to specifically detect the characteristic of the sample.

In some embodiments, suitable structural components for the exemplary optical computing devices disclosed herein are described in commonly owned U.S. Pat. Nos. 6,198,531; 6,529,276; 7,123,844; 7,834,999; 7,911,605, 7,920,258, and 8,049,881, each of which is incorporated herein by reference in its entirety, and U.S. patent application Ser. No. 12/094,460 (U.S. Pat. App. Pub. No. 2009/0219538); and Ser. No. 12/094,465 (U.S. Pat. App. Pub. No. 2009/0219539), each of which is also incorporated herein by reference in its entirety. As will be appreciated, variations of the structural components of the optical computing devices described in the above-referenced patents and patent applications may be suitable, without departing from the scope of the disclosure, and therefore, should not be considered limiting to the various embodiments disclosed herein.

The optical computing devices described in the foregoing patents and patent applications combine the advantage of the power, precision and accuracy associated with laboratory spectrometers, while being extremely rugged and suitable for field use. Furthermore, the optical computing devices can perform calculations (analyses) in real-time or near real-time without the need for sample processing. In this regard, the optical computing devices can be specifically configured to detect and analyze particular characteristics and/or analytes of interest. As a result, interfering signals are discriminated from those of interest in a sample by appropriate configuration of the optical computing devices, such that the optical computing devices provide a rapid response regarding the characteristics of the sample as based on the detected output. In some embodiments, the detected output can be converted into a voltage that is distinctive of the magnitude of the characteristic being monitored in the sample. The foregoing advantages and others make the optical computing devices, and their variations generally described below, particularly well suited for field and downhole use.

The exemplary optical computing devices described herein can be configured to detect not only the composition and concentrations of a material or mixture of materials, but they also can be configured to determine physical properties and other characteristics of the material as well, based on their analysis of the electromagnetic radiation received from the sample. For example, the optical computing devices can be configured to determine the concentration of an analyte and correlate the determined concentration to a characteristic of a substance by using suitable processing means. As will be appreciated, the optical computing devices may be configured to detect as many characteristics or analytes as desired in a given sample. All that is required to accomplish the monitoring of multiple characteristics or analytes is the incorporation of suitable processing and detection means within the optical computing device for each characteristic or analyte. In some embodiments, the properties of a substance can be a combination of the properties of the analytes therein (e.g., a linear, non-linear, logarithmic, and/or exponential combination). Accordingly, the more characteristics and analytes that are detected and analyzed using the exemplary optical computing devices, the more accurately the properties of the given sample can be determined.

The optical computing devices disclosed herein utilize electromagnetic radiation to perform calculations, as opposed to the hardwired circuits of conventional electronic processors. When electromagnetic radiation interacts with a substance, unique physical and chemical information about the substance may be encoded in the electromagnetic radiation that is reflected from, transmitted through, or radiated from the sample. This information is often referred to as the substance's spectral "fingerprint." At least in some embodiments, the exemplary optical computing devices disclosed herein are capable of extracting the information of the spectral fingerprint of multiple characteristics or analytes within a substance and converting that information into a detectable output regarding the overall properties of a sample. That is, through suitable configurations of the exemplary optical computing devices, electromagnetic radiation associated with characteristics or analytes of interest in a substance can be separated from electromagnetic radiation associated with all other components of a sample in order to estimate the sample's properties in real-time or near real-time.

The at least two processing elements used in the exemplary optical computing devices described herein may be characterized as integrated computational elements (ICE). The ICE are capable of distinguishing electromagnetic radiation related to the characteristic or analyte of interest from electromagnetic radiation related to other components of a sample substance. Referring to FIG. 1, illustrated is an exemplary ICE 100 suitable for use in the various optical computing devices described herein, according to one or more embodiments. As illustrated, the ICE 100 may include a plurality of alternating layers 102 and 104, such as silicon (Si) and $SiO_2$ (quartz), respectively. In general, these layers consist of materials whose index of refraction is high and low, respectively. Other examples might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be other types of optical substrates, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like. At the opposite end (e.g., opposite the optical substrate 106), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of the sample substance using a conventional spectroscopic instrument. The spectrum of interest of a given characteristic of a sample typically includes any number of different wavelengths. It should be understood that the exemplary ICE 100 in FIG. 1 does not in fact represent any particular characteristic of a given sample, but is provided for purposes of illustration only. Consequently, the number of layers 102, 104 and their relative thicknesses, as shown in FIG. 1, bear no correlation to any particular characteristic of a given sample. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$)

may vary, depending on the application, cost of materials, and/or applicability of the material to the sample substance.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), and/or acousto-optic elements, for example, that can create transmission, reflection, and/or absorptive properties of interest.

The multiple layers 102, 104 exhibit different refractive indices. By properly selecting the materials of the layers 102, 104 and their relative spacing, the exemplary ICE 100 may be configured to selectively pass/reflect/refract predetermined fractions of electromagnetic radiation at different wavelengths. Each wavelength is given a predetermined weighting or loading factor. The thicknesses and spacing of the layers 102, 104 may be determined using a variety of approximation methods from the spectrograph of the character or analyte of interest. These methods may include inverse Fourier transform (IFT) of the optical transmission spectrum and structuring the ICE 100 as the physical representation of the IFT. The approximations convert the IFT into a structure based on known materials with constant refractive indices. Further information regarding the structures and design of exemplary integrated computational elements (also referred to as multivariate optical elements) is provided in *Applied Optics*, Vol. 35, pp. 5484-5492 (1996) and Vol. 129, pp. 2876-2893, which is hereby incorporated by reference.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic or analyte of interest. Further details regarding how the exemplary ICE 100 is able to distinguish and process electromagnetic radiation related to the characteristic or analyte of interest are described in U.S. Pat. Nos. 6,198,531; 6,529,276; and 7,920,258, previously incorporated herein by reference.

Figure 2:
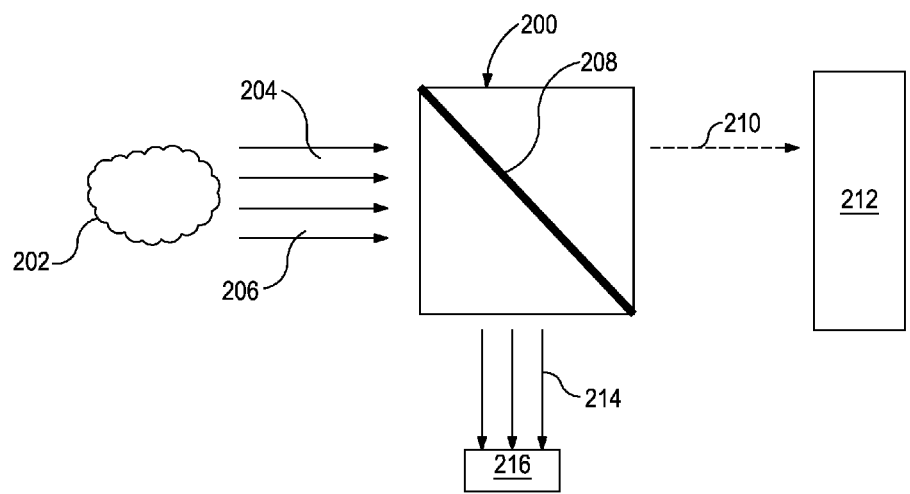
FIG. 2 illustrates a block diagram non-mechanistically illustrating how an optical computing device distinguishes electromagnetic radiation related to a characteristic of interest from other electromagnetic radiation, according to one or more embodiments.

Referring now to FIG. 2, illustrated is a block diagram that non-mechanistically illustrates how an optical computing device 200 is able to distinguish electromagnetic radiation related to a characteristic of a sample from other electromagnetic radiation. As shown in FIG. 2, after being illuminated with incident electromagnetic radiation, a sample 202 containing an analyte of interest (e.g., a characteristic of the sample) produces an output of electromagnetic radiation (e.g., sample-interacted light), some of which is electromagnetic radiation 204 corresponding to the characteristic or analyte of interest and some of which is background electromagnetic radiation 206 corresponding to other components or characteristics of the sample 202. Although not specifically shown, one or more spectral elements may be employed in the device 200 in order to restrict the optical wavelengths and/or bandwidths of the system and thereby eliminate unwanted electromagnetic radiation existing in wavelength regions that have no importance. Such spectral elements can be located anywhere along the optical train, but are typically employed directly after the light source, which provides the initial electromagnetic radiation. Various configurations and applications of spectral elements in optical computing devices may be found in commonly owned U.S. Pat. Nos. 6,198,531; 6,529,276; 7,123,844; 7,834,999; 7,911,605, 7,920,258, 8,049,881, and U.S. patent application Ser. No. 12/094,460 (U.S. Pat. App. Pub. No. 2009/0219538); Ser. No. 12/094,465 (U.S. Pat. App. Pub. No. 2009/0219539), incorporated herein by reference, as indicated above.

The beams of electromagnetic radiation 204, 206 impinge upon the optical computing device 200, which contains an exemplary ICE 208 therein. The ICE 208 may be configured to produce optically interacted light, for example, transmitted optically interacted light 210 and reflected optically interacted light 214. In at least one embodiment, the ICE 208 may be configured to distinguish the electromagnetic radiation 204 from the background electromagnetic radiation 206.

The transmitted optically interacted light 210, which may be related to the characteristic or analyte of interest, may be conveyed to a detector 212 for analysis and quantification. In some embodiments, the detector 212 is configured to produce an output signal in the form of a voltage that corresponds to the particular characteristic of the sample 202. In at least one embodiment, the signal produced by the detector 212 and the concentration of the characteristic of the sample 202 may be directly proportional. In other embodiments, the relationship may be a polynomial function, an exponential function, and/or a logarithmic function. The reflected optically interacted light 214, which may be related to the characteristic and other components of sample 202, can be directed away from detector 212. In alternative configurations, the ICE 208 may be configured such that the reflected optically interacted light 214 can be related to the analyte of interest, and the transmitted optically interacted light 210 can be related to other components of the sample 202.

In some embodiments, a second detector 216 can be present and arranged to detect the reflected optically interacted light 214. In other embodiments, the second detector 216 may be arranged to detect the electromagnetic radiation 204, 206 derived from the sample 202 or electromagnetic radiation directed toward or before the sample 202. Without limitation, the second detector 216 may be used to detect radiating deviations stemming from an electromagnetic radiation source (not shown), which provides the electromagnetic radiation (i.e., light) to the device 200. For example, radiating deviations can include such things as, but not limited to, intensity fluctuations in the electromagnetic radiation, interferent fluctuations (e.g., dust or other interferents passing in front of the electromagnetic radiation source), coatings on windows included with the optical computing device 200, combinations thereof, or the like. In some embodiments, a beam splitter (not shown) can be employed to split the electromagnetic radiation 204, 206, and the transmitted or reflected electromagnetic radiation can then be directed to one or more ICE 208. That is, in such embodiments, the ICE 208 does not function as a type of beam splitter, as depicted in FIG. 2, and the transmitted or reflected electromagnetic radiation simply passes through the ICE 208, being computationally processed therein, before travelling to the detector 212.

The characteristic(s) of the sample being analyzed using the optical computing device 200 can be further processed computationally to provide additional characterization information about the substance being analyzed. In some embodiments, the identification and concentration of each analyte in the sample 202 can be used to predict certain physical characteristics of the sample 202. For example, the bulk characteristics of a sample 202 can be estimated by using a combination of the properties conferred to the sample 202 by each analyte.

In some embodiments, the concentration of each analyte or the magnitude of each characteristic determined using the optical computing device 200 can be fed into an algorithm operating under computer control. The algorithm may be configured to make predictions on how the characteristics of the sample 202 change if the concentrations of the analytes are changed relative to one another. In some embodiments, the algorithm can produce an output that is readable by an operator who can manually take appropriate action, if needed, based upon the output. In some embodiments, the algorithm can take proactive process control by automatically adjusting the characteristics of, for example, a treatment fluid being introduced into a subterranean formation or by halting the introduction of the treatment fluid in response to an out of range condition.

The algorithm can be part of an artificial neural network configured to use the concentration of each detected analyte in order to evaluate the characteristic(s) of the sample 202 and predict how to modify the sample 202 in order to alter its properties in a desired way. Illustrative but non-limiting artificial neural networks are described in commonly owned U.S. patent application Ser. No. 11/986,763 (U.S. Patent Application Publication 2009/0182693), which is incorporated herein by reference. It is to be recognized that an artificial neural network can be trained using samples having known concentrations, compositions, and/or properties, thereby generating a virtual library. As the virtual library available to the artificial neural network becomes larger, the neural network can become more capable of accurately predicting the characteristics of a sample having any number of analytes present therein. Furthermore, with sufficient training, the artificial neural network can more accurately predict the characteristics of the sample, even in the presence of unknown analytes.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMs, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site.

Figure 3:
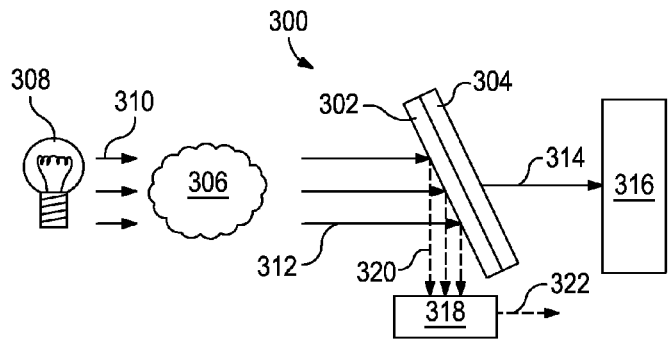
FIG. 3 illustrates an exemplary optical computing device, according to one or more embodiments.

Referring now to FIG. 3, illustrated is an exemplary optical computing device 300, according to one or more embodiments. The device 300 may be somewhat similar to the optical computing device 200 described above in FIG. 2, and therefore may be best understood with reference thereto. The device 300 may include at least two ICEs, illustrated as a first ICE 302 and a second ICE 304. The first and second ICE 302, 304 may be generally similar in construction to the ICE 100 described above with reference to FIG. 1, but may also vary from each other depending on the application, as will be better understood from the discussion below. In operation, the first and second ICE 302, 304 may enhance sensitivities and detection limits of the device 300 beyond what would be otherwise capable with a single ICE design. As will be appreciated, and discussed in greater detail below, two or more ICEs may be used in alternative configurations or embodiments, without departing from the scope of the disclosure.

In one embodiment, the first and second ICE 302, 304 may be configured to be associated with a particular characteristic of a sample 306. In other words, the first and second ICE 302, 304 may be especially designed in their respective layers, thicknesses, and materials so as to correspond with the spectral attributes associated with the characteristic of interest. Each of the first and second ICE 302, 304, however, may be designed entirely different from each other, thereby approximating or otherwise mimicking the regression vector of the characteristic in entirely different ways.

In other embodiments, however, one or both of the first and second ICE 302, 304 may not necessarily be configured to be associated with a particular characteristic of the sample 306, but instead may be entirely or substantially disassociated with the characteristic of interest. For example, manufacturing an ICE can be a very complex and intricate process. In addition, when an ICE is manufactured specifically to match or mimic the regression vector of a characteristic of interest, this process can become even more complicated. As a result, it is common to produce non-predictive, or poorly made ICE that, when tested, fail to accurately or even remotely be associated with the characteristic of interest. In some cases, these non-predictive ICE may return an arbitrary regression vector when tested or otherwise exhibit an arbitrary transmission function. In other cases, the non-predictive ICE may be considered "substantially" disassociated with the characteristic of interest in that the ICE only slightly mimics the regression vector of the characteristic, but is nonetheless considered non-predictive. In yet other cases, the non-predictive ICE may return a regression vector that closely mimics another characteristic of the substance being tested, but not the characteristic of interest.

As shown, the first and second ICE 302, 304 may be coupled together so as to form a generally monolithic structure. For example, the first and second IC 302, 304 may be mechanically or adhesively attached. In other embodiments, however, the first and second ICE 302, 304 may be arranged in series. For example, optically interacted light generated by the first ICE 302 may be received by the second ICE 304 in embodiments where the first and second ICE 302, 304 are separated in series by a nominal distance. The nominal distance can be anywhere from a few microns to several feet, and even further, depending on the size of the optical computing device 300. In at least one embodiment, the first ICE 302 may reflect optically interacted light to be subsequently received by the second ICE 304. In other embodiments, however, the first ICE 302 may transmit (i.e., allow to pass through) optically interacted light to be subsequently received by the second ICE 304. It should also be recognized that any of the ensuing configurations for optical computing devices can be used in combination with a series configuration in any of the present embodiments.

In FIG. 3, an electromagnetic radiation source 308 may be configured to emit or otherwise generate electromagnetic radiation 310. The electromagnetic radiation source 308 may be any device capable of emitting or generating electromagnetic radiation, as defined herein. In some embodiments, the electromagnetic radiation source 308 is a light bulb, light emitting device (LED), laser, blackbody, photonic crystal, or X-Ray source, or the like. In one embodiment, the electromagnetic radiation 310 may be configured to optically interact with the sample 306 and generate sample-interacted light 312 directed to the first and second ICE 302, 304. The sample 306 may be any fluid, as defined herein, or otherwise any solid substance or material such as, but not limited to, rock formations, concrete, or other solid surfaces. While FIG. 3 shows the electromagnetic radiation 310 as passing through the sample 306 to produce the sample-interacted light 312, it is also contemplated herein to reflect the electromagnetic radiation 310 off of the sample 306, such as in the case of a sample 306 that is translucent, opaque, or solid, and equally generate the sample-interacted light 312.

In the illustrated embodiment, the sample-interacted light 312 may be configured to optically interact with the first and second ICE 302, 304 and pass therethrough, thereby producing optically interacted light 314 that is directed to a detector 316. It should be noted that while FIG. 3 shows the sample-interacted light 312 as passing through the first and second ICE 302, 304 in order to generate the optically interacted light 314, it is also contemplated herein to reflect the sample-interacted light 312 off of the first and second ICE 302, 304 and equally generate the beam of optically interacted light 314. The detector 316 may be arranged to receive the optically interacted light 314 from the first and second ICE 302, 304 and generate a signal that corresponds to the particular characteristic of the sample 306. Similar to the detector 212 of FIG. 2, the detector 316 may be any device capable of detecting electromagnetic radiation, and may be generally characterized as an optical transducer. For example, the detector 316 may be, but is not limited to, a thermal detector such as a thermopile or photoacoustic detector, a semiconductor detector, a piezo-electric detector, charge coupled device (CCD) detector, video or array detector, split detector, photon detector (such as a photomultiplier tube), photodiodes, and/or combinations thereof, or the like, or other detectors known to those skilled in the art.

In at least one embodiment, the device 300 may include a second detector 318 arranged to receive and detect reflected optically interacted light 320 and thereby output a compensating signal 322. The second detector 318 may be substantially similar to the second detector 216 described above with reference to FIG. 2. Accordingly, the second detector 318 may detect radiating deviations stemming from the electromagnetic radiation source 308. In some embodiments, the second detector 318 may be arranged to receive a portion of the sample-interacted light 312 instead of the reflected optically interacted light 320, and thereby compensate for electromagnetic radiating deviations stemming from the electromagnetic radiation source 308. In yet other embodiments, the second detector 318 may be arranged to receive a portion of the electromagnetic radiation 310 instead of the reflected optically interacted light 320, and thereby likewise compensate for electromagnetic radiating deviations stemming from the electromagnetic radiation source 308.

We have discovered, in at least some embodiments, that using a combination of two or more ICE for the detection of a single characteristic of interest may result in substantially improved overall detection performance. This discovery was entirely unexpected. For example, U.S. Pat. No. 7,911,605 and U.S. Pat. Pub. No. 2010/0153048, incorporated herein by reference, describe in great detail how to design and build single ICE elements with optimal performance characteristics. Using the methods described in these references, literally thousands and hundreds of thousands of individual unique designs are created and optimized for performance, thereby exhausting the optimal solution space available and yielding the best solutions possible. Those skilled in the art will readily recognize that ICE elements can be particularly sensitive to small changes in their optical characteristics. Thus, any modification of the optical characteristic (e.g., changes made to the particular transmission function) with additional ICE elements, could be considered as degrading the performance of the optical computing device, and in most cases, quite rapidly with only small changes. Indeed, it has been discovered that some combinations of ICE components do degrade the overall performance of the optical computing device.

However, we have unexpectedly discovered that, in one or more embodiments, some preferred combinations of ICE can enhance performance and sensitivities. It has further been discovered that these enhancements are not minor adjustments or improvements, but instead may be able to enhance performance in what may be viewed as a dramatic way involving factors and/or orders of magnitude of improvement. It has yet further been discovered that such performance enhancements may be obtained without substantial compromise or trade-off of other important characteristics. In many embodiments, as briefly discussed above, each of the first and second ICE may be configured to be associated with the particular characteristic of the sample and serve to enhance sensitivities and detection limits of the device 300 beyond what would be otherwise capable with a single ICE design. However, we have unexpectedly discovered that embodiments where one or both of the first and second ICE are configured to be disassociated (or mainly disassociated) with the particular characteristic of the sample 306 may nonetheless serve to enhance the performance of the device 300 as compared to applications employing a single ICE to detect the same characteristic.

Figure 4:
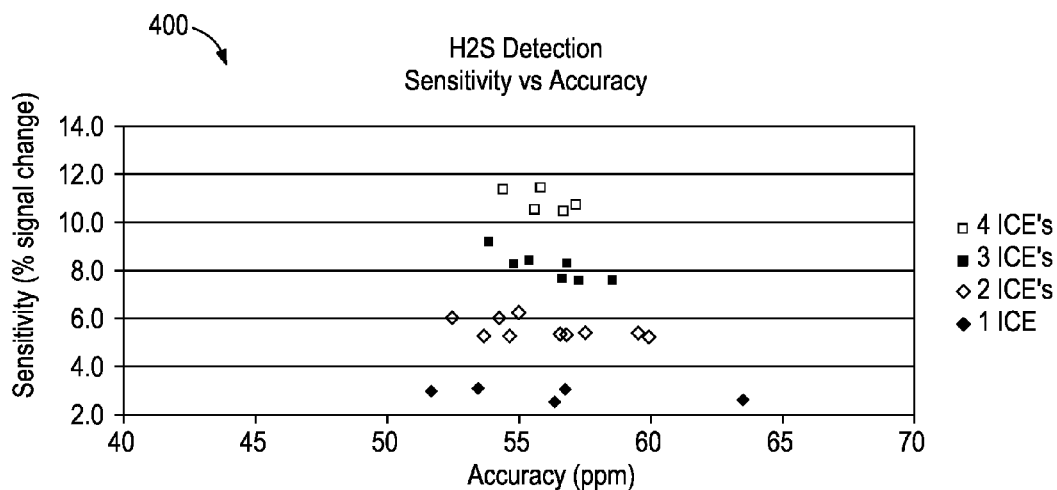
FIG. 4 illustrates a graph indicating the detection of a characteristic of interest in a sample using one or more integrated computational elements.

For example, referring to FIG. 4, illustrated is a graph 400 indicating the detection of a particular characteristic in a sample using one or more ICE components. It will be appreciated that the graph 400 and the data presented therein are merely used to facilitate a better understanding of the present disclosure, and in no way should the they be read to limit or define the scope of the invention. The graph 400 indicates the detection of hydrogen disulfide ($H_2S$) gas as the characteristic of interest from concentrations ranging between 0 and 1000 parts per million (ppm) in the presence of air and various concentrations of mercaptan (ranging from 50 to 150 ppm, benzene (ranging from 20 to 60 ppm), thiophene (ranging from 12 to 36 ppm) and toluene (ranging from 6 to 18 ppm). The X-axis of the graph 400 indicates the accuracy (standard deviation) of measuring the concentration of $H_2S$ across the entire 0 to 1000 ppm concentration range of interest in the presence of various concentrations and combinations of the above-noted gases for an optical computing device (e.g., the device 300). This was done for various single ICE designs and combinations of two or more ICE designs. As depicted, a single ICE design results in an accuracy ranging between about 50 ppm and about 65 ppm, depending upon the specific design selected. In the example, five distinct single ICE designs generally corresponding to the $H_2S$ characteristic were tested and the results recorded in the graph 400.

The sensitivity of the device, another key performance attribute that is vitally important to the detection limits, is also shown in the graph 400 on the Y-axis. The units of sensitivity are the % change in the detector signal output as expected over the entire $H_2S$ concentration range (i.e., 0 to 1000 ppm) of interest. Regarding sensitivity, the larger the % change, the more sensitive and desirable is the system as greater sensitivity can enable better detectability and performance limits, lower costs, and other important benefits. When two distinct ICEs are used to detect the same characteristic of interest, however, the graph 400 unexpectedly indicates that the sensitivity of the resulting signal may increase to a level approximately two-fold better. As depicted, there were up to ten different ICE combinations that were able to yield this dramatic improvement (while other combinations, as noted earlier, were observed to degrade the overall performance).

The graph 400 further indicates that employing a combination of three ICEs to detect the same characteristic may increase the sensitivity approximately three-fold over the single ICE design(s). Specifically, using a combination of three ICEs, arranged either linearly or non-linearly, returned or otherwise reported a sensitivity of 8% change in signal over the entire $H_2S$ concentration range of interest. This three-fold improvement was seen for eight different combinations out of all those possible amongst five different unique designs. Lastly, employing a combination of four ICEs to detect the same characteristic was shown to increase the sensitivity of the resulting signal approximately four-fold over the representative single ICE designs. Specifically, using a combination of four ICEs, either linearly or non-linearly, may be able to return a sensitivity of about 11% change in signal over the entire $H_2S$ concentration range of interest. This approximate four-fold increase was obtained for five different combinations out of all those possible amongst the five different unique designs. Accordingly, combining two or more ICEs may, in at least some embodiments, be able to increase the sensitivity of optical computing devices, such as, but not limited to, those specifically described herein.

Those skilled in the art will readily recognize that increases in sensitivity are often accompanied by corresponding decreases in accuracy for single ICE solutions. Thus, one single ICE design may have superior sensitivity over another, but may generally be found to be less accurate. Accuracy and sensitivity are two of the most important performance parameters for optical computing devices, and are thus generally considered trade-offs to one another. The improvement discovered and shown in FIG. 4 was entirely unexpected. Even more unexpected was that the sensitivity was dramatically increased in some cases without substantial trade-off in accuracy. For example, the single ICE solution exhibited accuracies ranging from 63.5 ppm to 51.7 ppm with an average of 56.4 ppm. The comparable numbers for the two ICE, three ICE, and four ICE solutions are, respectively, 52.5 to 60 ppm (56.1 ppm average); 53.9 to 58.6 ppm (56.1 ppm average); and 54.4 to 57.1 ppm (55.9 ppm average). Thus, in general contrast to the single ICE applications, sensitivity may be increased using two or more ICE components without experiencing a substantial or significant trade-off in accuracy.

Figure 5:
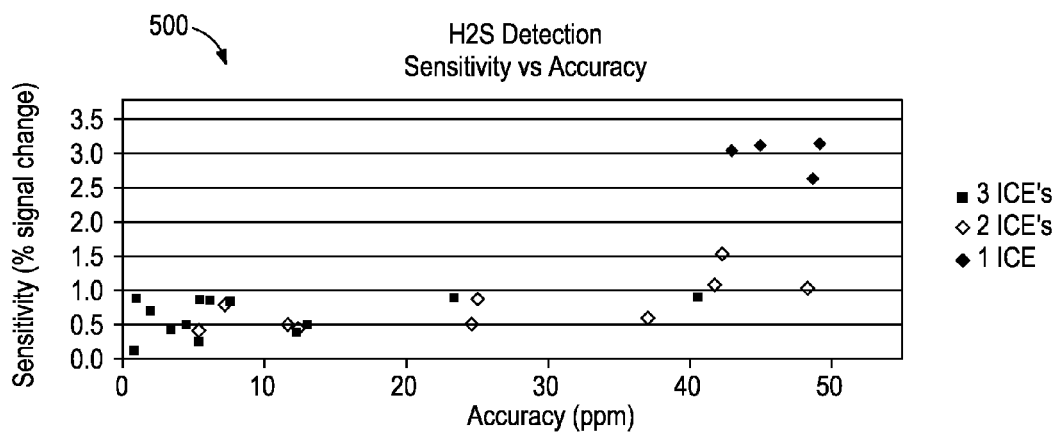
FIG. 5 illustrates another graph indicating the detection of a characteristic of interest in a sample using one or more integrated computational elements.

Referring to FIG. 5, illustrated is another graph 500 indicating the detection of $H_2S$ (i.e., the characteristic of interest) in a sample using one or more ICE components. As with the graph 400 of FIG. 4, the graph 500 and the data presented therein are used to facilitate a better understanding of the present disclosure, and in no way should the they be read to limit or define the scope of the invention. The graph 500 indicates the detection of $H_2S$ gas from concentrations ranging from 0 to 1000 ppm in the presence of air and various concentrations of mercaptan (ranging from 50 to 150 ppm), benzene (ranging from 20 to 60 ppm), and toluene (ranging from 6 to 18 ppm). The X-axis of the graph 500 depicts the accuracy (standard deviation) of measuring the concentration of $H_2S$ across the entire 0 to 1000 ppm concentration range of interest in the presence of various concentrations and combinations of the above-noted gases for an optical computing device (e.g., the device 300). This was done for various single ICE designs and combinations of two or more ICE designs. As shown, a single ICE design can provide an accuracy ranging between about 43 ppm and about 49 ppm, depending upon the specific design selected of the five distinct designs shown.

The graph 500 further indicates that employing a combination of up to three ICEs to detect the same characteristic may increase the accuracy as compared to the single ICE design(s). Specifically, using a combination of two ICEs, arranged either linearly or non-linearly, may increase accuracy down from an average of about 46 ppm to about 5.4 ppm, essentially gaining an improvement of about 8.5 times. Moreover, a combination of three ICEs may improve accuracy from an average of about 46 ppm down to about 1 ppm, or essentially gaining an improvement of about 46 times. Accordingly, combining two or more ICEs may, in at least some embodiments, increase the accuracy of optical computing devices, such as, but not limited to, those specifically described herein.

As noted above, it has been typically found that increases in sensitivity are generally accompanied by decreases in accuracy for single ICE solutions. Thus, one single ICE design may have superior sensitivity over another, but will generally be found to be less accurate. Thus, the improvements obtained and depicted in FIG. 5 for three ICE designs were entirely unexpected. Even more unexpected was that the accuracy, in at least some cases, increased with a reasonably small trade-off in sensitivity. For example, the single ICE solution as shown exhibited sensitivities ranging from 2.65 to 3.2%, with an average around 3%. At least three ICE combination designs improved the accuracy from an average of about 46 ppm down to about 1 ppm, resulting in 0.85% sensitivity. In other words, in this case accuracy was improved about 46-fold with only a 3.5-fold decrease in sensitivity. Accordingly, in general contrast to the single ICE applications, accuracy may be increased without experiencing an unreasonable or significant trade-off in sensitivity.

In the exemplary cases depicted above in FIGS. 4 and 5, each of the ICEs were designed to detect the particular characteristic of interest (i.e., $H_2S$). However, increases in both sensitivity and accuracy may also be obtained, in at least some cases, when at least one of the two or more ICE components is disassociated or otherwise substantially unrelated to the characteristic of interest. For example, Table 1 below indicates the detection of $H_2S$ gas from concentrations ranging between 0 and 1000 ppm in the presence of air and various concentrations of mercaptan (ranging from 50 to 150 ppm), benzene (ranging from 20 to 60 ppm), thiophene (ranging from 12 to 36 ppm), and toluene (ranging from 6 to 18 ppm).

TABLE 1

$H_2S$ Detection with Various ICE

| | Total # ICE | Accuracy (standard deviation) (ppm) | Notes |
|---|---|---|---|
| ICE #1 Alone (substantially disassociated with $H_2S$) | 1 | 144 | Marginally predictive |
| Plus ICE #2 (disassociated with $H_2S$) | 2 | 67 | Predictive |
| Plus ICE #3 (disassociated with $H_2S$) | 3 | 38 | Highly predictive |

Figure 6:
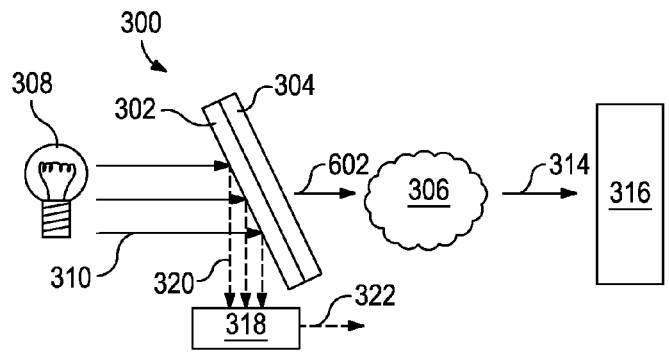
FIG. 6 illustrates another exemplary optical computing device, according to one or more embodiments.

Table 1 depicts the accuracy (standard deviation) of measuring the concentration of $H_2S$ across the entire 0 to 1000 ppm range using multiple ICE that are disassociated with $H_2S$. In particular, ICE #1 is substantially disassociated with $H_2S$ and demonstrates or otherwise reports an accuracy of 144 ppm which, as can be appreciated by those skilled in the art, may be considered as only slightly better than a random guess. However, combining ICE #1 with ICE #2, which was considered entirely disassociated with $H_2S$, unexpectedly improved the accuracy from 144 ppm down to 67 ppm, or slightly more than two-fold. Combining ICE #1, ICE #2, and ICE #3 (where ICE #3 is also considered entirely disassociated with $H_2S$) improved the accuracy even further down to 38 ppm, or slightly less than four-fold over the single ICE #1 result of 144 ppm. Accordingly, substantial and unexpected performance can be obtained even using ICEs that are disassociated or substantially disassociated with the characteristic of interest. Referring now to FIG. 6, with continued reference to FIG. 3, illustrated is another embodiment of the optical computing device 300, according to one or more embodiments. As illustrated, the sample 306 may be arranged after the first and second ICE 302, 304, such that the electromagnetic radiation 310 is directly received by the first and second ICE 302, 304 and optically interacted light 602 is thereafter directed to the sample 306. As depicted, the detector 316 still receives optically interacted light 314, albeit from the sample 306 instead of from the first and second ICE 302, 304. Accordingly, it matters not in what order the sample 306 and first and second ICE 302, 304 optically interact with the electromagnetic radiation 310, as long as each component is able to do so before the resulting optically interacted light 314 (i.e., including optical interaction with both the sample 306 and the first and second ICE 302, 304) is eventually directed to the detector 316. Moreover, it will be appreciated that while FIG. 6 shows the electromagnetic radiation 310 passing through the first and second ICE 302, 304 in order to optically interact with the sample 306, the electromagnetic radiation 310 could equally be reflected off the first and second ICE 302, 304 toward the sample 306. Likewise, while FIG. 6 shows the optically interacted light 602 passing through the sample 306, the optically interacted light 602 could equally be reflected off of the sample 306 and subsequently detected by the detector 316, without departing from the scope of the disclosure. Furthermore, embodiments are contemplated herein that include one or more optional beam splitters, mirrors, and the like in order to allow the electromagnetic radiation 310 to optically interact with both the sample 306 and first and second ICE 302, 304, without departing from the scope of the disclosure. Indeed, one or more optional beam splitters, mirrors, and the like may be used in conjunction with any of the exemplary embodiments disclosed herein, without departing from the scope of the disclosure.

Consequently, it should be understood that even though the electromagnetic radiation 310 may optically interact with the sample 306 before reaching the first and second ICE 302, 304, the first and second ICE 302, 304 nonetheless are considered to have optically interacted with the electromagnetic radiation 310, albeit subsequent to the sample 306. Likewise, even though the electromagnetic radiation 310 may optically interact with the first and second ICE 302, 304 before reaching the sample 306, the sample 306 nonetheless is considered to have optically interacted with the electromagnetic radiation 310, albeit subsequent to the first and second ICE 302, 304. Furthermore, embodiments are contemplated herein where the first ICE 302 is arranged on one side of the sample 306, and the second ICE 304 is arranged on the opposite side of the sample 306. As a result, the electromagnetic radiation 310 may optically interact with the first ICE 302 prior to optically interacting with the sample 306, and subsequently optically interacting with the second ICE 304. The resulting optically interacted light 314 directed to the detector 316 may nonetheless be similar to embodiments where the first and second ICE 302, 304 are arranged either before or after the sample 306. Moreover, it will be appreciated that any and all of the embodiments disclosed herein may include any of the exemplary variations discussed herein, such as arranging the sample 306 before or after the ICE 302, 304, or arranging the ICE 302, 304 in linear or non-linear configurations. While not particularly disclosed, several variations of the embodiments disclosed herein will equally fall within the scope of the disclosure.

Figure 7:
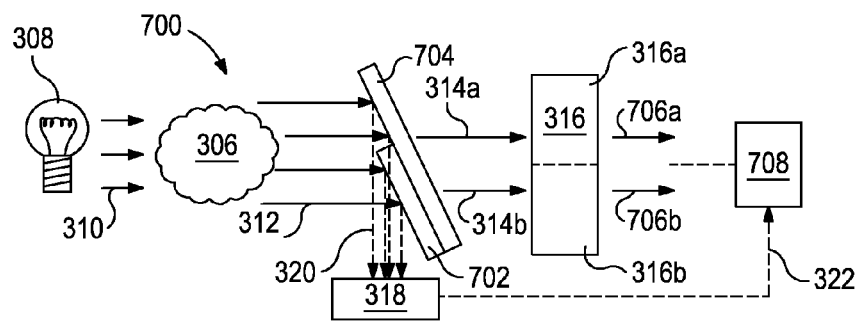
FIG. 7 illustrates another exemplary optical computing device, according to one or more embodiments.

Referring now to FIG. 7, illustrated is another embodiments of an optical computing device 700 disclosed herein, according to one or more embodiments. The device 700 may be best understood with reference to FIGS. 3 and 6, where like numerals indicate like elements that will not be described again in detail. The device 700 may include a first ICE 702 and a second ICE 704. The first and second ICE 702, 704 may be similar in construction to the ICE 100 described above with reference to FIG. 1, and configured to be either associated or disassociated with a particular characteristic of the sample, such as is described above with reference to the first and second ICE 302, 304 of FIGS. 3 and 6.

As illustrated, the first and second ICE 702, 704 may be coupled together to form a monolithic structure, but in other embodiments may be arranged in series, as briefly discussed above, without departing from the scope of the disclosure. Moreover, the first and second ICE 702, 704 may be arranged to receive sample-interacted light 312, as depicted, but may equally be arranged antecedent to the sample 306, as generally described above with reference to FIG. 6. In one embodiment, the first ICE 702 may be smaller than the second ICE 704 such that a portion of the sample-interacted light 312 (or portion of the electromagnetic radiation 310, in the event the sample 306 is arranged on the other side of the first and second ICE 702, 704) passes through only the second ICE 704 and generates a first beam of optically interacted light 314a, and another portion of the sample-interacted light 312 passes through both the first and second ICE 702, 704 and thereby generates a second beam of optically interacted light 314b.

The first and second beams of optically interacted light 314a,b may be directed to the detector 316, which may be a split or differential detector, having a first detector portion 316a and a second detector portion 316b. In other embodiments, however, the detector 316 may be a detector array, as known in the art, without departing from the scope of the disclosure. In operation, the first detector portion 316a may be configured to receive the first beam of optically interacted light 314a and generate a first signal 706a, and the second detector portion 316b may be configured to receive the second beam of optically interacted light 314b and generate a second signal 706b. In some embodiments, the detector 316 may be configured to computationally combine the first and second signals 706a,b in order to determine the characteristic of the sample, for example when using a differential detector or quad-detector. In other embodiments, the first and second signals 706a,b may be transmitted to or otherwise received by a signal processor 708 communicably coupled to the detector 316 and configured to computationally combine the first and second signals 706a,b in order to determine the characteristic of the sample. In some embodiments, the signal processor 708 may be a computer including a non-transitory machine-readable medium, as generally described above.

In at least one embodiment, the device 700 may further include the second detector 318 arranged to receive and detect reflected optically interacted light 320, as generally described above with reference to FIG. 3. As described above, the second detector 318 may be used to detect electromagnetic radiating deviations exhibited by the electromagnetic radiation source 308, and thereby normalize the signal output of the first detector 316. In at least one embodiment, the second detector 318 may be communicably coupled to the signal processor 708 such that the compensating signal 322 indicative of electromagnetic radiating deviations may be provided or otherwise conveyed thereto. The signal processor 708 may then be configured to computationally combine the compensating signal 322 with the first and second signals 706a,b, and thereby provide a more accurate determination of the characteristic of the sample. In one embodiment, for example, the compensating signal 322 is combined with the first and second signals 706a,b via principal component analysis techniques such as, but not limited to, standard partial least squares which are available in most statistical analysis software packages (e.g., XL Stat for MICROSOFT® EXCEL®; the UNSCRAMBLER® from CAMO Software and MATLAB® from MATHWORKS®).

Figure 8:
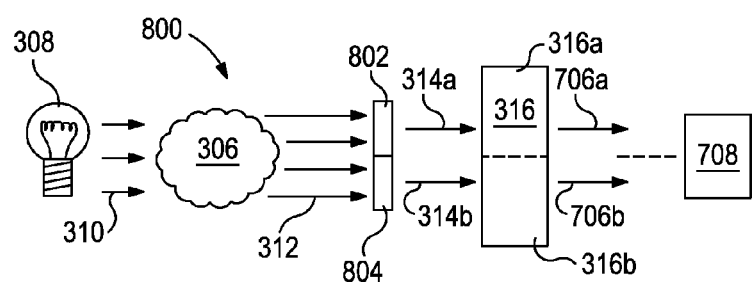
FIG. 8 illustrates another exemplary optical computing device, according to one or more embodiments.

Referring now to FIG. 8, with continued reference to FIG. 7, illustrated is another optical computing device 800, according to one or more embodiments. The device 800 may be somewhat similar to the optical computing device 700 described with reference to FIG. 7, therefore the device 800 may be best understood with reference thereto, where like numerals indicate like elements. The device 800 may include a first ICE 802 and a second ICE 804 similar in construction to the ICE 100 described above with reference to FIG. 1, and configured to be either associated or disassociated with a particular characteristic of the sample 306, such as is described above with reference to the first and second ICE 302, 304 of FIGS. 3 and 6.

As illustrated, the first and second ICE 802, 804 may be arranged generally parallel relative to one another and configured to receive the sample-interacted light 312. As with prior embodiments, however, the first and second ICE 802, 804 may equally be arranged antecedent to the sample 306, as generally described above with reference to FIG. 6, without departing from the scope of the disclosure. In operation, the first ICE 802 may receive a portion of the sample-interacted light 312 (or portion of the electromagnetic radiation 310, in the event the sample 306 is arranged on the other side of the first and second ICE 802, 804) and thereby generate the first beam of optically interacted light 314a. The second ICE 804 may be configured to receive another portion of the sample-interacted light 312 and thereby generate the second beam of optically interacted light 314b. The first and second beams of optically interacted light 314a,b may be directed to the detector 316 to generate the first signal 706a and the second signal 706b corresponding to the first and second beams of optically interacted light 314a,b, respectively.

The first detector portion 316a may be configured to receive the first beam of optically interacted light 314a and generate the first signal 706a, and the second detector portion 316b may be configured to receive the second beam of optically interacted light 314b and generate the second signal 706b. In some embodiments, the detector 316 may be configured to computationally combine the first and second signals 706a,b in order to determine the characteristic of the sample. In other embodiments, however, the first and second signals 706a,b may be received by a signal processor 708 communicably coupled to the detector 316 and configured to computationally combine the first and second signals 706a,b in order to determine the characteristic of the sample.

In some embodiments, the detector 316 is a single detector but configured to time multiplex the first and second beams of optically interacted light 314a,b. For example, the first ICE 802 may be configured to direct the first beam of optically interacted light 314a toward the detector 316 at a first time T1, and the second ICE 804 may be configured to direct the second beam of optically interacted light 314b toward the detector 316 at a second time T2, where the first and second times T1, T2 are distinct time periods that do not spatially overlap. Consequently, the detector 316 receives at least two distinct beams of optically interacted light 314a,b, which may be computationally combined by the detector 316 in order to provide an output in the form of a voltage that corresponds to the characteristic of the sample. In one or more embodiments, in order to provide the first and second times T1, T2, the device 800 may include more than one electromagnetic radiation source 308. In other embodiments, the electromagnetic radiation source 308 may be pulsed in order to provide the first and second times T1, T2. In yet other embodiments, each ICE 802, 804 may be mechanically positioned to interact with the electromagnetic radiation beam at two distinct times. In yet other embodiments, the electromagnetic radiation beam may be deflected, or diffracted to interact with the two different ICE elements at times T1 and T2. Moreover, it will be appreciated that more than the first and second ICE 802, 804 may be used without departing from the scope of this embodiment, and the detector 316 may therefore be configured to time multiplex each additional beam of optically interacted light to provide the cumulative voltage corresponding to the characteristic of the sample.

Figure 9A:
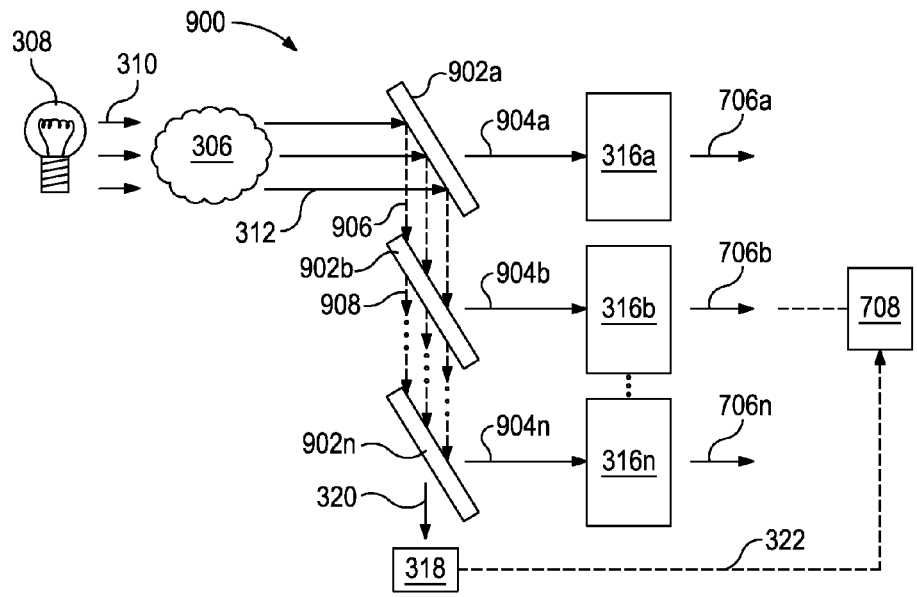
FIGS. 9a, 9b, and 9c illustrate other exemplary optical computing devices, according to one or more embodiments.

Referring now to FIG. 9a, illustrated is another optical computing device 900, according to one or more embodiments. The device 900 may be somewhat similar to the optical computing devices 700, 800 described with reference to FIGS. 7 and 8 and therefore the device 900 may be best understood with reference thereto, where like numerals indicate like elements. The device 900 may include at least two ICE, including a first ICE 902a and a second ICE 902b, and may further include one or more additional ICE 902n. Each ICE 902a-n may be similar in construction to the ICE 100 described above with reference to FIG. 1, and configured to be either associated or disassociated with a particular characteristic of the sample 306, such as is described above with reference to the first and second ICE 302, 304 of FIGS. 3 and 6. The device 900 may further include a plurality of detectors, such as a first detector 316a, a second detector 316b, and one or more additional detectors 316n.

As illustrated in FIG. 9a, the first, second, and additional ICE 902a-n may each be arranged in series relative to one another and configured to optically interact with the electromagnetic radiation 312 either through the sample 306 or through varying configurations of reflection and/or transmission between adjacent ICE 902a-n. In the embodiment specifically depicted, the first ICE 902a may be arranged to receive the sample-interacted light 312 from the sample 306. As with prior embodiments, however, the first ICE 902a may equally be arranged antecedent to the sample 306, as generally described above with reference to FIG. 6, and therefore optically interact with the electromagnetic radiation 310. The first ICE 902a may be configured to transmit a first optically interacted light 904a to the first detector 316a and simultaneously convey reflected optically interacted light 906 toward the second ICE 902b. The second ICE 902b may be configured to convey a second optically interacted light 904b via reflection toward the second detector 316b, and simultaneously transmit additional optically interacted light 908 toward the additional ICE 902n. The additional ICE 902n may be configured to convey an additional optically interacted light 904n via reflection toward the additional detector 316n. Those skilled in the art will readily recognize numerous alternative configurations of the first, second, and additional ICE 902a-n, without departing from the scope of the disclosure. For example, reflection of optically interacted light from a particular ICE may be replaced with transmission of optically interacted light, or alternatively configurations may include the use of mirrors or beam splitters configured to direct the electromagnetic radiation 310 (or sample-interacted light 312) to each of the first, second, and additional ICE 902a-n.

The first, second, and additional detectors 316a-n may be configured to detect the first, second, and additional optically interacted light 904a-n, respectively, and thereby generate a first signal 706a, a second signal 706b, and one or more additional signals 706n, respectively. In some embodiments, the first, second, and additional signals 706a-n may be received by a signal processor 708 communicably coupled to each detector 316a-n and configured to computationally combine the first, second, and additional signals 706a-n in order to determine the characteristic of the sample 306.

Accordingly, any number of ICE may be arranged or otherwise used in series in order to determine the characteristic of the sample 306. In some embodiments, each of the first, second, and additional ICE 902a-n may be specially-designed to detect the particular characteristic of interest or otherwise be configured to be associated therewith. In other embodiments, however, one or more of the first, second, and additional ICE 902a-n may be configured to be disassociated with the particular characteristic of interest, and/or otherwise may be associated with an entirely different characteristic of the sample 306. In yet other embodiments, each of the first, second, and additional ICE 902a-n may be configured to be disassociated with the particular characteristic of interest, and otherwise may be associated with an entirely different characteristic of the sample 306.

In at least one embodiment, the device 900 may further include the second detector 318 arranged to receive and detect optically interacted light 320, as generally described above with reference to FIG. 3. The second detector 318 may again be used to detect electromagnetic radiating deviations exhibited by the electromagnetic radiation source 308 and output the compensating signal 322 indicative of electromagnetic radiating deviations. In at least one embodiment, the second detector 318 may be communicably coupled to the signal processor 708 such that the compensating signal 322 may be provided or otherwise conveyed thereto in order to normalize the signals 706a-n produced by the detectors 316a-n. The signal processor 708 may then be configured to computationally combine the compensating signal 322 with the signals 706a-n, and thereby provide a more accurate determination of the characteristic of the sample.

Figure 9B:
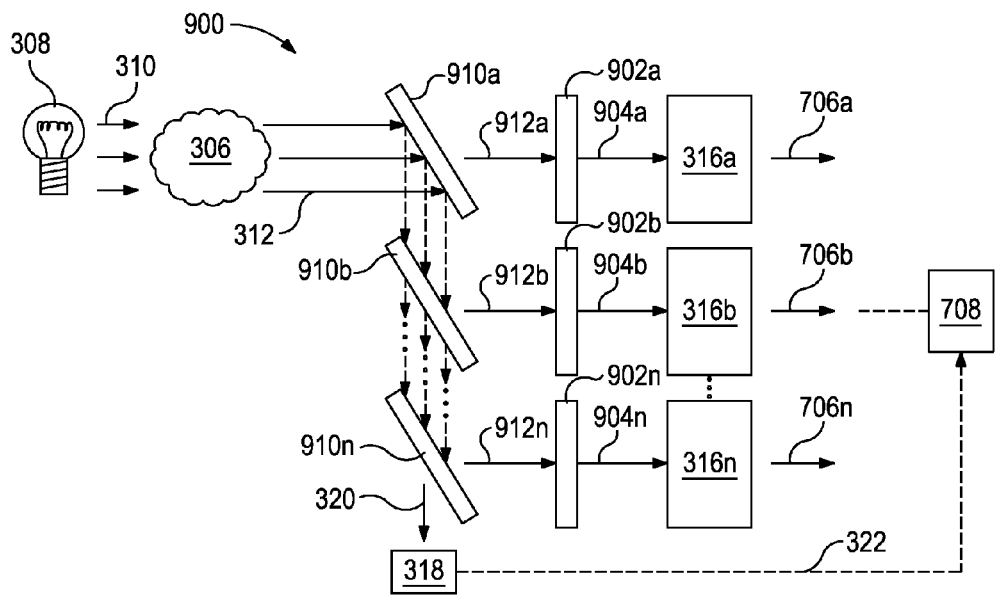

Referring now to FIG. 9b, illustrated is an alternative configuration of the optical computing device 900, according to one or more embodiments. In FIG. 9b, a series of beam splitters 910a, 910b, 910n may be used to separate or otherwise redirect the sample-interacted light 312 As depicted, each beam splitter 910a-n may be configured to produce and direct a respective beam 912a, 912b, 912n of sample-interacted light 312 toward a corresponding ICE 902a-n. Each ICE 902a-n may then be configured to transmit its respective optically interacted light 904a-n toward a corresponding detector 316a-n, thereby generating the first, second, and additional signals 706a-n, respectively. The first, second, and additional signals 706a-n may then be received by a signal processor 708 communicably coupled to each detector 316a-n and configured to computationally combine the first, second, and additional signals 706a-n in order to determine the characteristic of the sample 306.

In some embodiments, the second detector 318 may again be used to detect electromagnetic radiating deviations exhibited by the electromagnetic radiation source 308, and thereby normalize the signals 706a-n produced by the detectors 316a-n. The second detector 318 may be communicably coupled to the signal processor 708 such that the compensating signal 322 indicative of electromagnetic radiating deviations may be provided or otherwise conveyed thereto. The signal processor 708 may then be configured to computationally combine the compensating signal 322 with the signals 706a-n, and thereby normalize the signals 706a-n and provide a more accurate determination of the characteristic of the sample 306.

Figure 9C:
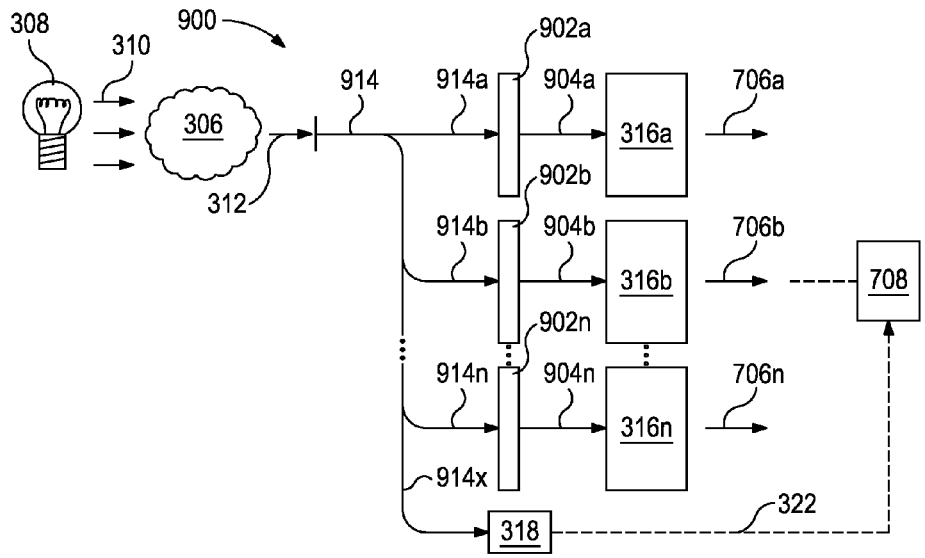

Referring now to FIG. 9c, illustrated is yet another alternative configuration of the optical computing device 900, according to one or more embodiments. As illustrated in FIG. 9c, the sample-interacted light 312 may be fed into or otherwise provided to, for example, an optical light pipe 914. The optical light pipe may be configured to convey the sample-interacted light 312 individually to each ICE 902a-n. In some embodiments, the optical light pipe 914 may be a fiber optic bundle having a plurality of corresponding conveying bundles. In operation, a first bundle 914a may be configured to convey sample-interacted light 312 to the first ICE 902a in order to generate the first optically interacted light 904a; a second bundle 914b may be configured to convey sample-interacted light 312 to the second ICE 902b in order to generate the second optically interacted light 904b; and an additional bundle 914n may be configured to convey sample-interacted light 312 to the additional ICE 902n in order to generate the additional optically interacted light 904n. At least one additional bundle 914x may be configured to convey sample-interacted light 312 to the second detector 318 in order to generate the compensating signal 322. Processing of the resulting optically interacted light 904a-n and signals 706a-n may be accomplished as generally described above.

It should be noted that the use of optical light pipes, such as the optical light pipe 914 discussed above, may be employed in any of the various embodiments discussed herein, without departing from the scope of the disclosure. Use a light pipe, or a variation thereof, may prove advantageous in that the light pipe substantially removes interferent obstruction that may otherwise contaminate the sample-interacted light 312 provided to the various ICEs.

Figure 10:
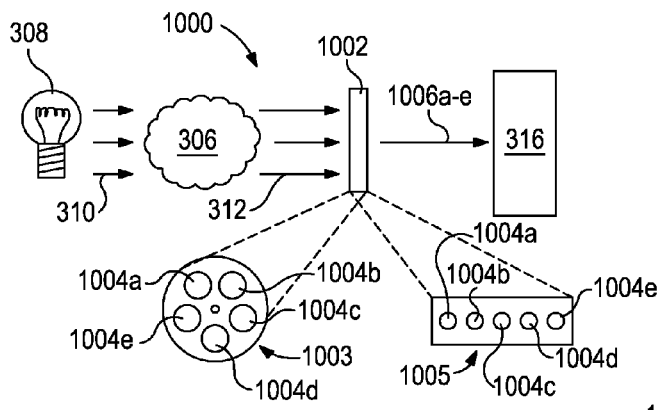
FIG. 10 illustrates another exemplary optical computing device, according to one or more embodiments.

Referring now to FIG. 10, illustrated is another optical computing device 1000, according to one or more embodiments. The device 1000 may be somewhat similar to the optical computing device 300 described with reference to FIGS. 3 and 6 and therefore the device 1000 may be best understood with reference thereto, where like numerals indicate like elements. The device 1000 may include a movable assembly 1002 having at least two ICEs associated therewith. As illustrated, the movable assembly 1002 may be characterized at least in one embodiment as a rotating disc 1003, wherein the at least two ICEs are radially disposed for rotation therewith. Alternatively, the movable assembly 1002 may be characterized as a linear array 1005, wherein the at least two ICEs are laterally offset from each other. FIG. 10 illustrates corresponding frontal views of the rotating disc 1003 and the linear array 1005, each of which is described in more detail below.

Those skilled in the art will readily recognize, however, that the movable assembly 1002 may be characterized as any type of movable assembly configured to sequentially align at least one detector with optically interacted light and/or one or more ICE. For example, the movable assembly 1002 may include such apparatus or devices as, but not limited to, an oscillating or translating linear array of ICE, one or more scanners, one or more beam deflectors, combinations thereof, or the like. In other embodiments, the movable assembly 1002 may be characterized as an assembly including a plurality of optical light pipes (e.g., fiber optics) configured to perform optical beam splitting to a fixed array of ICE and/or detectors.

The rotating disc 1003 may include a first ICE 1004a, a second ICE 1004b, a third ICE 1004c, a fourth ICE 1004d, and a fifth ICE 1004e arranged about or near the periphery of the rotating disc 1003 and circumferentially-spaced from each other. Each ICE 1004a-e may be similar in construction to the ICE 100 described above with reference to FIG. 1, and configured to be either associated or disassociated with a particular characteristic of the sample 306, such as is described above with reference to the first and second ICE 302, 304 of FIGS. 3 and 6. In various embodiments, the rotating disc 1003 may be rotated at a frequency of about 0.1 RPM to about 30,000 RPM. In operation, the rotating disc 1003 may rotate such that the individual ICEs 1004a-e may each be exposed to or otherwise optically interact with the sample-interacted light 312 for a distinct brief period of time. In at least one embodiment, however, the movable assembly 1002 may be arranged antecedent to the sample 306, as generally described above with reference to FIG. 6, such that the individual ICEs 1004a-e of the rotating disc 1003 may be exposed to or otherwise optically interact with the electromagnetic radiation 310 for a brief period of time. Upon optically interacting with the sample-interacted light 312 (or the electromagnetic radiation 310, in the event the sample 306 is arranged subsequent to the movable assembly 1002), each ICE 1004a-e may be configured to produce optically interacted light, for example, a first beam of optically interacted light 1006a, a second beam of optically interacted light 1006b, a third beam of optically interacted light 1006c, a fourth beam of optically interacted light 1006d, and a fifth beam of optically interacted light 1006e, respectively.

Each beam of optically interacted light 1006a-e may be detected by the detector 316 which may be configured to time multiplex the optically interacted light 1006a-e between the individually-detected beams. For example, the first ICE 1004a may be configured to direct the first beam of optically interacted light 1006a toward the detector 316 at a first time T1, the second ICE 1004b may be configured to direct the second beam of optically interacted light 1006b toward the detector 316 at a second time T2, and so on until the fifth ICE 1004e may be configured to direct the fifth beam of optically interacted light 1006e toward the detector 316 at a fifth time T5. Consequently, the detector 316 receives at least five distinct beams of optically interacted light 1006a-e, which may be computationally combined by the detector 316 in order to provide an output in the form of a voltage that corresponds to the characteristic of the sample. In some embodiments, these beams of optically interacted light 1006a-e may be averaged over an appropriate time domain (e.g., about 1 millisecond to about 1 hour) to more accurately determine the characteristic of the sample 306.

In one or more embodiments, at least one of the ICE 1004a-e may be a neutral element configured to simply pass the sample-interacted light 312 (or the electromagnetic radiation 310, in the event the sample 306 is arranged subsequent to the movable assembly 1002) without optical-interaction. As a result, the neutral element may be configured to provide a neutral signal to the detector 316 that may be substantially similar to the compensating signal 322 as described above with reference to FIG. 3. In operation, the detector 316 may detect the neutral signal, which may be indicative of radiating deviations stemming from the electromagnetic radiation source 308. The detector 316 may then be configured to computationally combine the compensating signal 322 with the remaining beams of optically interacted light 1006a-e to compensate for electromagnetic radiating deviations stemming from the electromagnetic radiation source 308, and thereby provide a more accurate determination of the characteristic of the sample.

As will be appreciated, any number of ICE 1004a-e may be radially arranged on the rotating disc 1003 in order to determine the characteristic of the sample 306. In some embodiments, each of the ICE 1004a-e may be specially-designed to detect or otherwise configured to be associated with the particular characteristic of interest. In other embodiments, however, one or more of the ICE 1004a-e may be configured to be disassociated with the particular characteristic of interest, and otherwise may be associated with an entirely different characteristic of the sample 306. Advantages of this approach may include the ability to analyze multiple analytes using a single optical computing device and the opportunity to assay additional analytes simply by adding additional ICEs to the rotating disc 1003.

The linear array 1005 may also include the first, second, third, fourth, and fifth ICE 1004a-e, although aligned linearly as opposed to radially. The linear array 1005 may be configured to oscillate or otherwise translate laterally such that each ICE 1004a-e is exposed to or otherwise able to optically interact with the sample-interacted light 312 for a distinct brief period of time. Similar to the rotating disc 1003, the linear array 1005 may be configured to produce optically interacted light 1006a-e. Moreover, as with the rotating disc 1003 embodiment, the detector 316 may be configured to time multiplex the optically interacted light 1006a-e between the individually-detected beams and subsequently provide an output in the form of a voltage that corresponds to the characteristic of the sample. Even further, at least one of the ICE 1004a-e may be a neutral element configured to provide a neutral signal to the detector 316 that may be computationally combined with the remaining beams of optically interacted light 1006a-e to compensate for electromagnetic radiating deviations stemming from the electromagnetic radiation source 308.

As will be appreciated, any number of ICE 1004a-e may be arranged on the linear array 1005 in order to determine the characteristic of the sample 306. In some embodiments, each of the ICE 1004a-e may be specially-designed to detect or otherwise configured to be associated with the particular characteristic of interest. In other embodiments, however, one or more of the ICE 1004a-e may be configured to be disassociated with the particular characteristic of interest, and otherwise may be associated with an entirely different characteristic of the sample 306. In yet other embodiments, each of the one or more ICE 1004a-e may be configured to be disassociated with the particular characteristic of interest, and otherwise may be associated with an entirely different characteristic of the sample 306.

Figure 11:
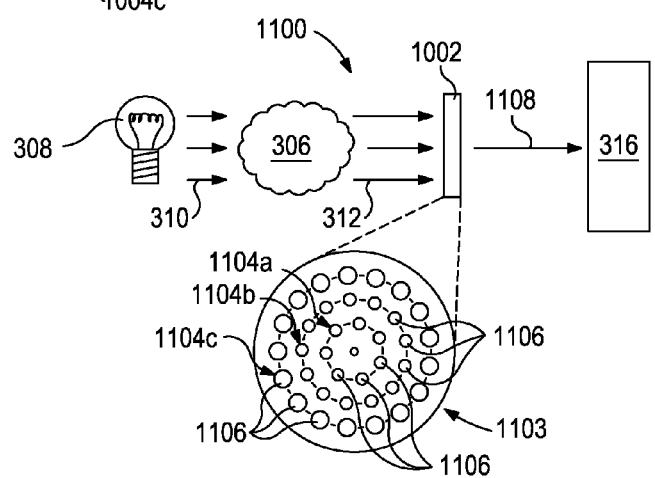
FIG. 11 illustrates another exemplary optical computing device, according to one or more embodiments.

Referring now to FIG. 11, with continued reference to FIG. 10, illustrated is another exemplary optical computing device 1100, according to one or more embodiments. The device 1100 may be somewhat similar to the device 1000 of FIG. 10, and therefore may be best understood with reference thereto where like numerals indicate like elements. The device 1100 may include a movable assembly 1102 similar in some respects to the movable assembly 1002 of FIG. 10. For example, FIG. 11 illustrates an alternative embodiment of a rotating disc 1103. The filter wheel 1103 in FIG. 11, however, may include multiple radially-offset rows or arrays of ICE, such as a first radial array 1104a, a second radial array 1104b, and a third radial array 1104c. While three radial arrays 1104a-c are shown in FIG. 11, it will be appreciated that the filter wheel 1103 may include more or less than three radially-offset radial arrays 1104a-c, without departing from the scope of the disclosure.

Each radially-offset radial array 1104a-c may include a plurality of ICEs 1106 circumferentially-spaced from each other. Each ICE 1106 may be similar in construction to the ICE 100 described above with reference to FIG. 1, and configured to be either associated or disassociated with a particular characteristic of the sample 306, such as is described above with reference to the first and second ICE 302, 304 of FIGS. 3 and 6. In operation, the filter wheel 1103 rotates such that the one or more ICEs 1106 may each be exposed to or otherwise optically interact with the sample-interacted light 312 for a distinct brief period of time. In at least one embodiment, however, the filter wheel 1103 may be arranged antecedent to the sample 306, as generally described above with reference to FIG. 6, and therefore the one or more ICEs 1106 may be exposed to or otherwise optically interact with the electromagnetic radiation 310 for a brief period of time. Upon optically interacting with the sample-interacted light 312 (or the electromagnetic radiation 310, in the event the sample 306 is arranged subsequent to the filter wheel 1103), each ICE 1106 may be configured to produce an individual or combined beam of optically interacted light 1108 directed toward the detector 316.

Each individual or combined beam of optically interacted light 1108 may be detected by the detector 316 which may be configured to time multiplex the optically interacted light 1108 between the combined or individually-detected beams. Consequently, the detector 316 receives a plurality of beams of optically interacted light 1108 which may be computationally combined by the detector 316 in order to provide an output in the form of a voltage that corresponds to the characteristic of the sample. Moreover, one or more of the ICE 1106 may be a neutral element configured to provide a neutral signal to the detector 316, as generally described above with reference to FIG. 10. The neutral signal may be indicative of radiating deviations stemming from the electromagnetic radiation source 308, and the detector 316 may be configured to computationally combine the neutral signal with the remaining beams of optically interacted light 1108 to compensate for electromagnetic radiating deviations stemming from the electromagnetic radiation source 308, and thereby provide a more accurate determination of the characteristic of the sample.

While the various embodiments disclosed herein provide that the electromagnetic radiation source 308 is used to provide electromagnetic radiation that optically interacts with the at least two ICEs, those skilled in the art will readily recognize that electromagnetic radiation may be derived from the sample 306 itself, and otherwise derived independent of the electromagnetic radiation source 308. For example, various substances naturally radiate electromagnetic radiation that is able to optically interact with the at least two ICEs. In some embodiments, the sample 306 may be a blackbody radiating substance configured to radiate heat that may optically interact with the at least two ICEs. In other embodiments, the sample 306 may be radioactive or chemo-luminescent and, therefore, radiate electromagnetic radiation that is able to optically interact with the at least two ICEs. In yet other embodiments, the electromagnetic radiation may be induced from the sample 306 by being acted upon mechanically, magnetically, electrically, combinations thereof, or the like. For instance, in at least one embodiment, a voltage may be placed across the sample 306 in order to induce the electromagnetic radiation. As a result, embodiments are contemplated herein where the electromagnetic radiation source 308 is omitted from the particular optical computing device.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method of determining a characteristic of a sample, comprising:
    optically interacting an electromagnetic radiation source with the sample to form input light for at least two integrated computational elements, wherein a first one of the at least two integrated computational elements comprises a first plurality of layers of material and a second one of the at least two integrated computational elements comprises a second plurality of layers of material different from the first plurality of layers of material, the first and second pluralities of layers of material being disposed according to the characteristic of the sample;
    producing optically interacted light from the at least two integrated computational elements, wherein the first and second plurality of layers of material are selected so that an intensity of the optically interacted light is proportional to a dot product between an input light spectrum vector and a regression vector associated with the characteristic of the sample;
    receiving with at least one detector the optically interacted light from the at least two integrated computational elements, thereby generating a first signal and a second signal; and
    computationally combining the first and second signals to determine the characteristic of the sample.

2. The method of claim 1, wherein the at least one detector computationally combines the first and second signals.

3. The method of claim 1, wherein the at least one detector is a first detector, the method further comprising:
    detecting with a second detector electromagnetic radiation from the electromagnetic radiation source;
    generating a third signal with the second detector, the third signal being indicative of electromagnetic radiating deviations;
    receiving the third signal with a signal processor communicably coupled to the first and second detectors; and
    computationally combining the third signal with the first and second signals to normalize the first and second signals.

4. The method of claim 1, further comprising rotating the at least two first and second integrated computational elements within a movable assembly configured for rotation, the at least two integrated computational elements being radially disposed within the movable assembly.

5. The method of claim 4, further comprising:
    optically interacting the electromagnetic radiation source with at least one neutral element radially disposed within the movable assembly for rotation therewith; and
    producing a compensating signal indicative of radiating deviations of the electromagnetic radiation source.

6. The method of claim 5, further comprising:
    receiving with the at least one detector the compensating signal; and
    computationally combining the compensating signal with the first and second signals in order to compensate for electromagnetic radiating deviations.

7. The method of claim 1, further comprising oscillating the at least two first and second integrated computational elements as arranged on a linear array.

8. A method of determining a characteristic of a sample, comprising:
    optically interacting an electromagnetic radiation source with the sample to form input light for at least two integrated computational elements, wherein a first one of the at least two integrated computational elements comprises a first plurality of layers of material and a second one of the at least two integrated computational elements comprises a second plurality of layers of material different from the first plurality of layers of material, the first and second pluralities of layers of material being disposed according to the characteristic of the sample;
    producing optically interacted light from the at least two integrated computational elements, wherein the first and second plurality of layers of material are selected so that an intensity of the optically interacted light is proportional to a dot product between an input light spectrum vector and a regression vector associated with the characteristic of the sample; and
    receiving with at least one detector the optically interacted light from the at least two integrated computational elements, thereby generating a first signal corresponding to the characteristic of the sample.

9. The method of claim 8, further comprising:
    detecting with a second detector electromagnetic radiation from the electromagnetic radiation source; and
    generating a second signal indicative of electromagnetic radiating deviations with the second detector.

10. The method of claim 9, further comprising:
    receiving the first and second signals with a signal processor communicably coupled to the first and second detectors; and
    computationally combining the first and second signals to normalize the first signal.

11. A method of determining a characteristic of a sample, comprising:

optically interacting electromagnetic radiation radiated from the sample with at least two integrated computational elements, wherein a first one of the at least two integrated computational elements comprises a first plurality of layers of material and a second one of the at least two integrated computational elements comprises a second plurality of layers of material different from the first plurality of layers of material, the first and second pluralities of layers of material disposed according to a characteristic of the sample;

producing optically interacted light from the at least two integrated computational elements, the at least two integrated computational elements each being configured to be associated with the characteristic of the sample, wherein the first and second plurality of layers of material are selected so that an intensity of the optically interacted light is proportional to a dot product between a spectrum vector of the electromagnetic radiation radiated from the sample and a regression vector associated with the characteristic of the sample; and receiving with at least one detector the optically interacted light from the at least two integrated computational elements, thereby generating a first signal corresponding to the characteristic of the sample.

12. The method of claim 11, further comprising acting upon the sample mechanically, magnetically, or electrically in order to emit the electromagnetic radiation from the sample.

* * * * *